US008801677B2

(12) United States Patent
Wallin

(10) Patent No.: US 8,801,677 B2
(45) Date of Patent: Aug. 12, 2014

(54) MEDICAL CLAMP FOR FLEXIBLE TUBING

(76) Inventor: Brandon Wallin, Logan, UT (US)

( * ) Notice: Subject to any disclaimer, the term of this patent is extended or adjusted under 35 U.S.C. 154(b) by 0 days.

(21) Appl. No.: 13/590,540

(22) Filed: Aug. 21, 2012

(65) Prior Publication Data

US 2013/0066280 A1 Mar. 14, 2013

Related U.S. Application Data

(60) Provisional application No. 61/534,523, filed on Sep. 14, 2011.

(51) Int. Cl.
*A61M 5/00* (2006.01)
*A61M 39/28* (2006.01)

(52) U.S. Cl.
CPC .................. *A61M 39/284* (2013.01)
USPC ................. 604/250; 251/9; 251/10

(58) Field of Classification Search
CPC ............................ A61M 39/28; A61M 39/284
USPC ........................................ 604/250; 251/9–10
See application file for complete search history.

(56) References Cited

U.S. PATENT DOCUMENTS

| 6,234,448 | B1 * | 5/2001 | Porat | 251/10 |
| 6,644,618 | B1 * | 11/2003 | Balbo | 251/10 |
| 2010/0152681 | A1 * | 6/2010 | Mathias | 604/250 |

* cited by examiner

*Primary Examiner* — Edelmira Bosques
(74) *Attorney, Agent, or Firm* — J. Todd Rushton

(57) ABSTRACT

A medical clamp having a semi-circular front engagement portion with reciprocal transverse grooves formed in the opposing clamp surface. The semi-circular engagement portion allows for easy alignment, safe operation and completely eliminates the possibility of misalignment and unintentional release.

6 Claims, 5 Drawing Sheets

MEDICAL CLAMP FOR FLEXIBLE TUBING

BACKGROUND

Tubing clamps are ubiquitous in the medical industry and tens of thousands are used each day in myriad applications such as flow control for IV bags, blood donor bags and even sealing the umbilical cord of a newborn. Varying sizes and types of tubing clamps may be used for different applications.

One of the most prevalent medical tubing clamps is the Halkey-Roberts type clamp. This clamp is effective for controlling blood flow to donation bags, for controlling or shutting-off flow in IV bags and for controlling dosage of intravenous drugs. The Halkey-Roberts type clamp has a laminar body, bent back onto itself in essentially a u-shape with, two apertures allowing the flexible tubing to be passed longitudinally through the clamp body and over two opposing cleats or bumps, two elastically opposing ends form a ratchet type latch, allowing the clamp to be closed and adjusted. The top portion of the ratchet type latch having a substantially straight front edge, the front edge is undercut forming an acute angle or knife edge. The front edge configured to engage a series of transverse slots arranged vertically on the inside face of the bottom portion of the clamp. The clamp is adjusted by forcing the top portion into the bottom portion, allowing the front edge of the top portion to engage a correspondingly lower transverse slot; as the top portion is depressed, the internal cleats crimp the flexible hose closed.

One issue with the Halkey-Roberts clamp is the lack of secure engagement when a side pressure is applied or if the clamp is misaligned when closing. The Halkey-Roberts clamp has no provision to prevent lateral movement or twisting of the latch. When the clamp is closed in a misaligned or twisted configuration there are at least two issues that arise. First, the clamp cleats do not close evenly, possibly resulting in uneven metering or not fully clamping a hose closed if the user desires to completely terminate flow. The second issue is the clamp may unintentionally release. When the front edge of the top portion is misaligned with the reciprocal transverse slot, only a corner of the front edge is engaging the slot, if the clamp is bumped or jarred, the clamp can completely release resulting in unrestricted fluid flow through the flexible tubing. In the case of drug metering, a clamp release could have catastrophic results.

Other clamps have attempted to remedy this situation with varying results, including, the clamp described in U.S. Pat. No. 6,644,618 to Balbo, filed Jun. 8, 2000 (hereinafter, the Balbo patent). The device of the Balbo patent includes a vertical rib protruding from the face of the top engagement portion and a corresponding slot integrated into the vertical face of the bottom engagement portion, when the clamp is closed at least a portion of the vertical rib is constrained in at least a portion of the corresponding slot. This arrangement significantly reduces the chance that a closed clamp can be forced into a misaligned position, however, it does not appear to prevent a user from closing a clamp unevenly, or under a torsional load, and at least partially closing the clamp with the vertical rib outside of the vertical slot. Additionally, the device of the Balbo patent with the engagement of the vertical rib and corresponding slot appears to introduce a possible "pinch point" that may cause injury to the user.

What is needed is a medical clamp that fully eliminates the possibility of misaligned engagement and is easy and safe to use.

SUMMARY OF THE INVENTION

The present invention is a medical clamp having a rounded or semi-circular front engagement portion with reciprocal transverse grooves, allowing for easy alignment, safe operation and eliminates possibility of misalignment and unintentional release.

One embodiment of the present invention is a medical clamp having body portion of substantially uniform thickness which is bent forming a complete rectangle, with rounded corners, when observed from a side view. The medical clamp having an aperture opening on each end, allowing one or more flexible tubes to be passed through, in a longitudinal direction, the flexible tubing passing over two opposing bumps or cleats designed to engage and crush the outside portion of the flexible tubing. The medical clamp of the present invention having an open engagement end including, opposing top and bottom portions, the top portion having a rounded or semi-circular front edge, the front edge being undercut to form an acute angle or "knife edge" configured to engage a series of semi-circular or radial transverse slots arranged in a vertical configuration on an inside vertical wall of the bottom portion. When the medical clamp of the present invention is deployed, the user will depress the top portion of the clamp into the bottom portion, the rounded front edge will progressively engage the corresponding transverse slots. As the top portion of the medical clamp is depressed, the opposing cleats engage the outside surface of the flexible tubing, progressively restricting fluid flow until the flow is completely shut off.

In one embodiment of the present invention, an alignment ramp precedes the semi-circular transverse slots. The alignment ramp progressively loads the inherent spring action of the clamp and aligns the semi-rounded front edge of the top portion with the semi-circular transverse slots in the bottom portion. The alignment ramp allows for easy engagement of the clamp and smooth operation. Easy engagement and smooth operation reduces the possibility of injury when using the medical clamp.

For another embodiment of the present invention the top portion of the clamp includes a thumb well or depression allowing the user to visually identify proper thumb position and reduce the possibility of slippage when closing the clamp.

In another embodiment of the present invention, the thumb depression is replaced with a texture pattern, which may include but is not limited to, ridges, cleats, slots, bumps or images.

In yet another embodiment of the present invention, the medical clamp includes a textured section on the bottom portion of the clamp diametrically opposed to the thumb depression. The textured section designed to engage the lateral side of the user's index finger when closing the clamp. The textured section provides a visual reference for the user when positioning the clamp in their hand and reduces the opportunity for slippage and possible injury.

In each embodiment to the present invention, the medical clamp is released from an engaged position by moving the bottom portion of the engagement section away from the semi-circular front edge of the top portion. The spring action of the medical clamp is biased toward an open position.

These and other features and advantages of the disclosure will be set forth and will become more fully apparent in the detailed description that follows and in the appended claims. The features and advantages may be realized and obtained by the instruments and combinations particularly pointed out in the appended claims. Furthermore, the features and advantages of the disclosure may be learned by the practice of the methods or will be obvious from the description, as set forth hereinafter.

The following description of the embodiments can be understood in light of the Figures, which illustrate specific aspects of the embodiments and are part of the specification.

Together with the following description, the Figures demonstrate and explain the principles of the embodiments. In the Figures the physical dimensions of the embodiment may be exaggerated for clarity. The same reference numerals in different drawings represent the same element, and thus their descriptions may be omitted.

DETAIL DESCRIPTION OF THE DRAWINGS

Figure 1:
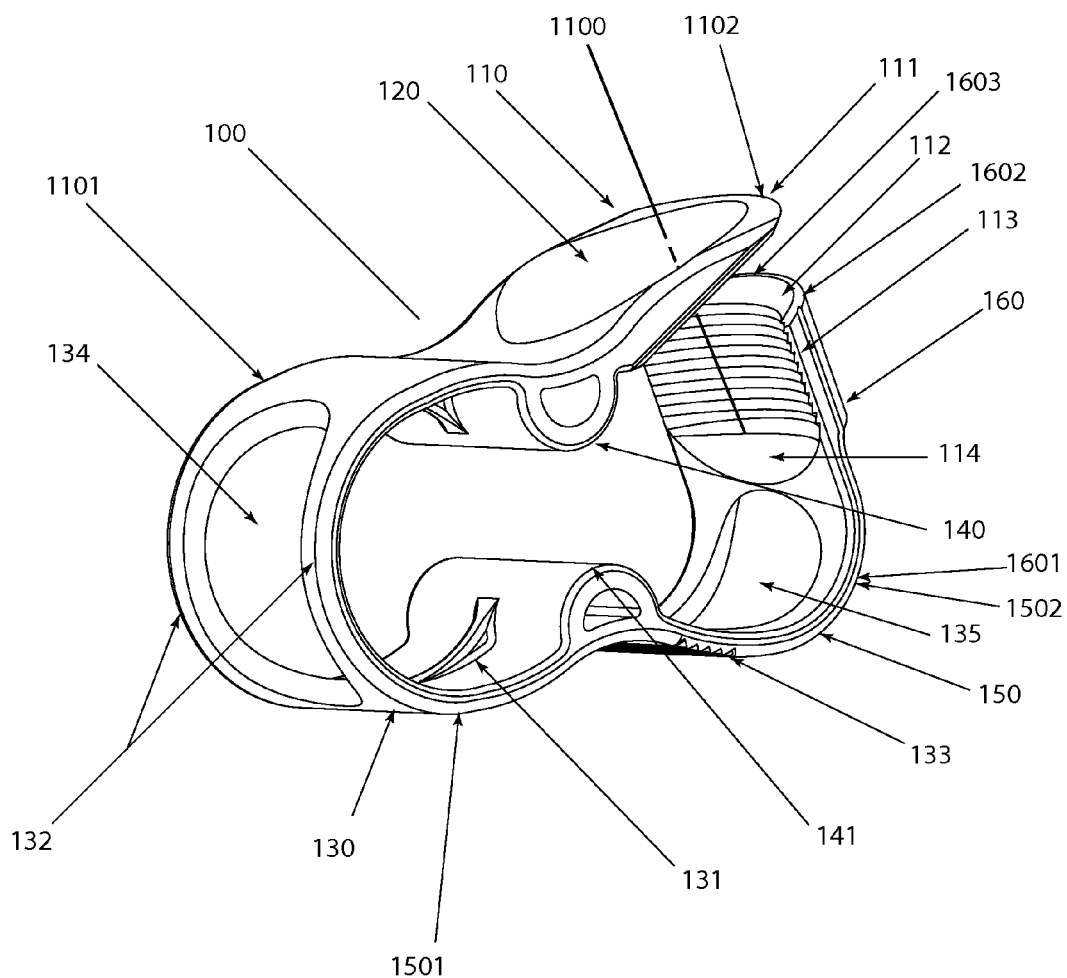
FIG. 1, is an orthogonal view of a medical clamp.
Figure 2:
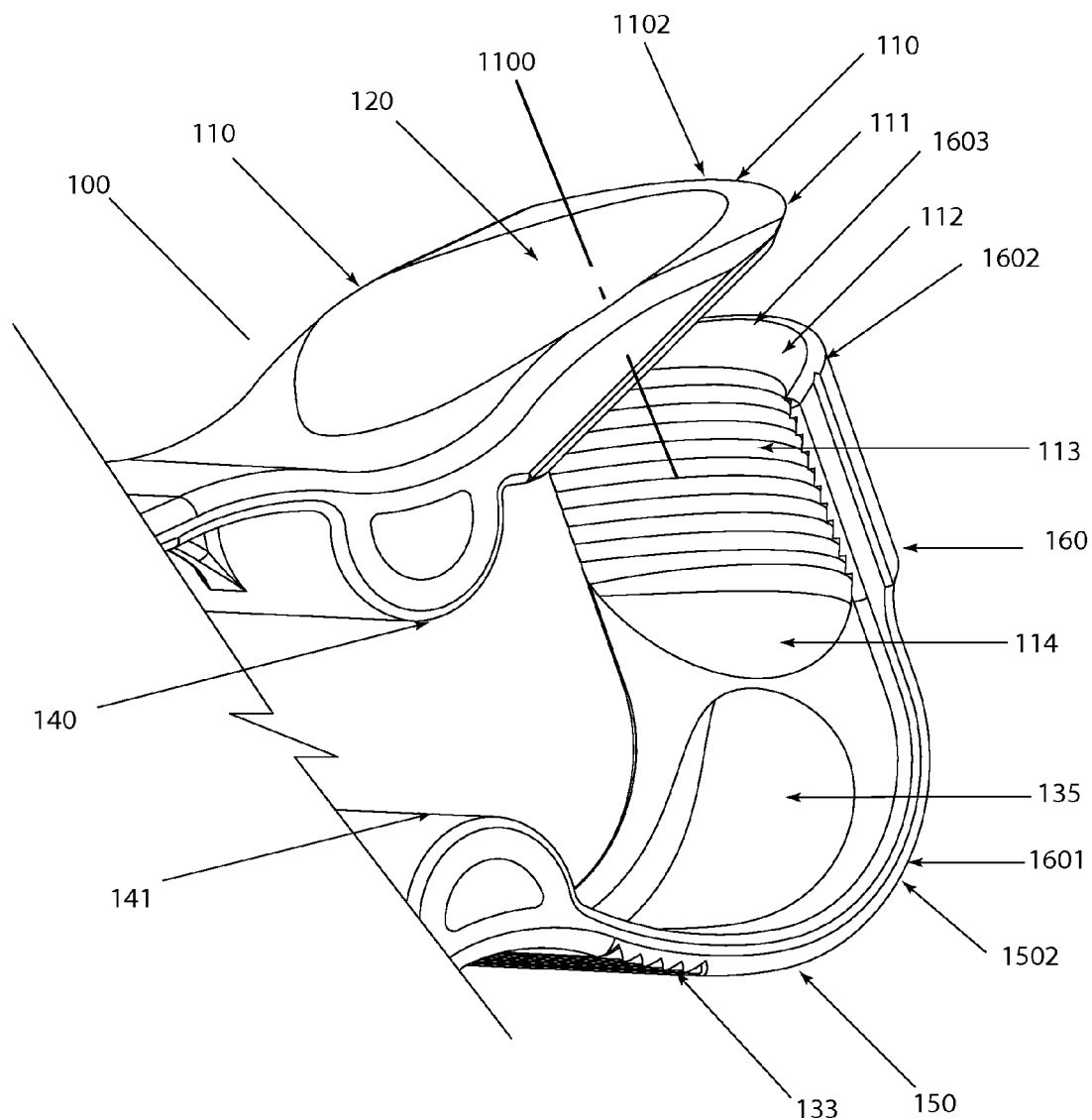
FIG. 2, is detailed view of the medical clamp engagement portion.
Figure 3:
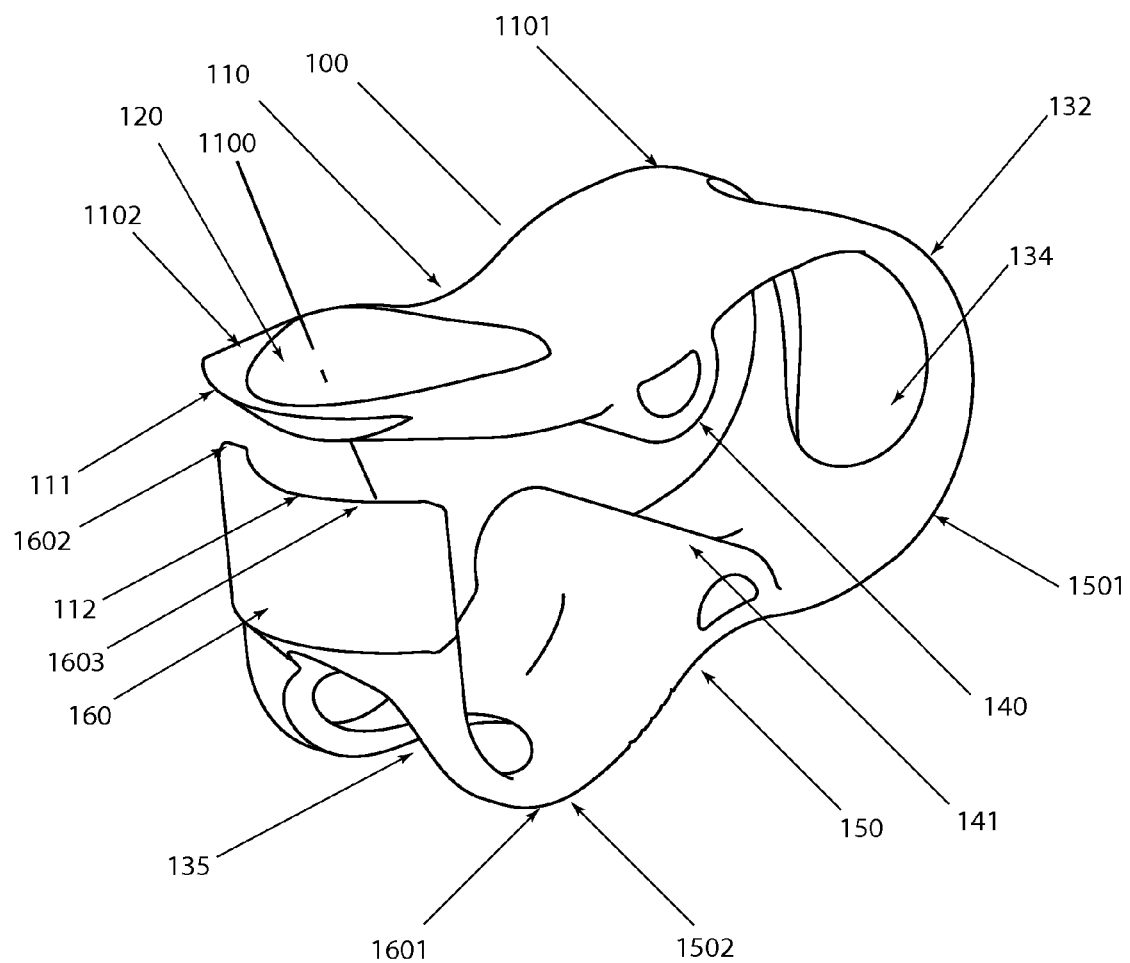
FIG. 3, is a front facing orthogonal view of a medical clamp.
Figure 4:
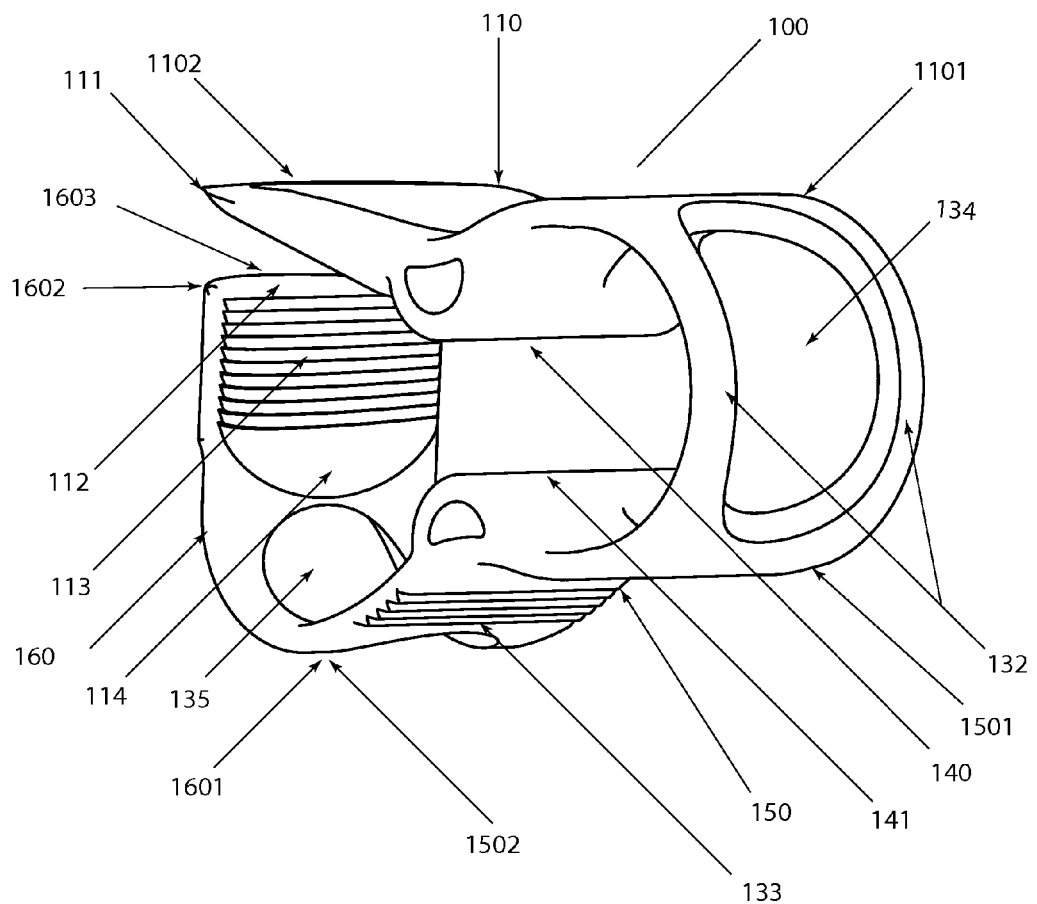
FIG. 4, is a rear facing orthogonal view of a medical clamp.
Figure 5:
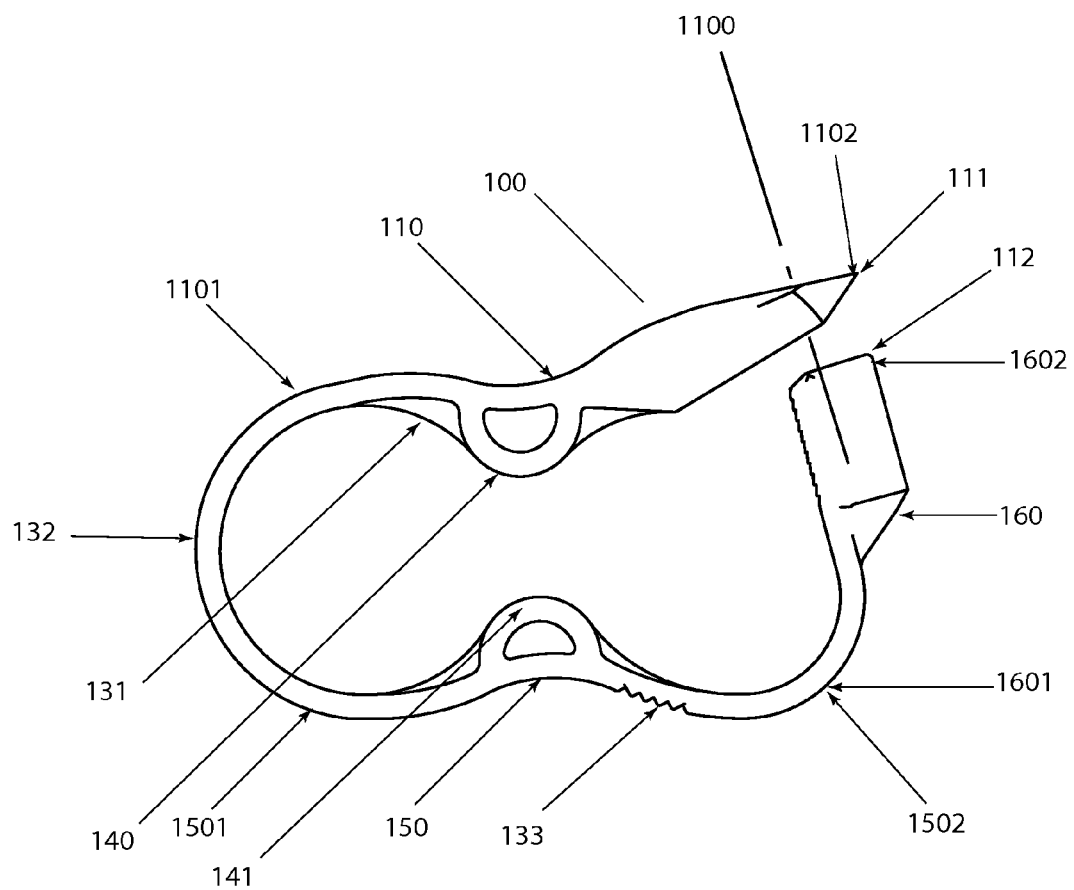
FIG. 5, is a side view of a medical clamp.

FIGS. 1 through 5 are one embodiment of the present invention, or an improved medical clamp 100 for flexible tubing. The medical clamp 100 including a spring section 132 having material of a substantially uniform thickness, the spring section 132 bent back on itself forming a u-shaped clamp body 130 when viewed from the side as shown in FIG. 5. The clamp body 130 having aperture openings in each end, including rear opening 134 and front opening 135, where one or more flexible tubes (not shown) can be passed through, the flexible tubing passes longitudinally between top cleat 140 and opposing bottom cleat 141, cleats 140 and 141 designed to engage the outside surface of the flexible tubing and can be positioned to restrict or shut off flow through the flexible tubing. One embodiment of the present invention includes stiffening ribs 131 which engage the sides of cleats 140 and 141 and clamp body 130. Medical clamp 100 is closed or adjusted by depressing the semi-circular leading edge 111 of the top portion 110 into vertically arranged reciprocal transverse slots 113. The distance between opposing cleats 140 and 141 is adjusted by moving the leading edge 111 into progressively lower transverse slots 113, as the distance between cleats 140 and 141 is reduced, flow through the flexible tubing is proportionally reduced until the flow is completely shut off. One embodiment of the present invention includes an alignment ramp 112 preceding the transverse slots 113. Alignment ramp 112 progressively displaces the spring action and opposing engagement between the top portion leading edge 111 and the bottom portion transverse slots 113. Alignment ramp 112 allows for smooth initial engagement between the leading edge 111 and the transverse slots 113. Transition section 114 acts as a bottom limit for leading edge 111 and allows for a smooth material transition between the semi-circular transverse slots 113 and the clamp body 130.

Medical clamp 100 includes; a top portion 110 having a first end 1101 attached to the spring section 132, and a second free end 1102. Semi-circular leading edge 111 formed in free end 1102 of top portion, 110, the semi-circular leading edge 111 having a central axis 1100 perpendicular to the outside surface of the top portion 110. A bottom portion 150 including a first end 1501 attached to the spring section 132 and a second end 1502. An engagement portion 160 including a first end 1601 attached to the second end 1502 of the bottom portion 150, and a free end 1602. A semi-circular engagement slot 1603 formed on the inside surface of the free end 1602 of engagement portion 160. Transverse slots 113 formed in engagement slot 1603.

One embodiment of the present invention includes a thumb depression 120 on the top portion of clamp body 130 and a textured finger pad 133 on the bottom portion of clamp 130. Both the thumb depression 120 and textured finger pad 133 are visual positioning guides for the user when operating the clamp 100 and reduce the chance of injury due to slipping.

It is to be understood that the above mentioned arrangements are only illustrative of the application of the principles of the present disclosure. Numerous modifications or alternative arrangements may be devised by those skilled in the art without departing from the spirit and scope of the present disclosure and the appended claims are intended to cover such modifications and arrangements. Thus, while the present disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

The invention claimed is:

1. A medical clamp assembly comprising: a unitary body forming generally a complete rectangle having rounded corners, the unitary body having, a top portion, a bottom portion, a spring portion and an engagement portion;

the top portion having a outside surface, a inside surface, a first end attached to the spring portion and a second free end;

the bottom portion having a outside surface, a inside surface, a first end attached to the spring portion and a second end attached to the engagement portion;

the engagement portion having a outside surface, a inside surface, a first end attached to the bottom portion and a second free end;

the free end of the top portion formed as a semi-circle having a central axis perpendicular to the outside surface and having a front edge tapered from the inside surface to the outside surface;

the inside surface of the free end of the engagement portion having an engagement slot formed as a semi-circle reciprocal to the semi-circle of the free end of the top portion;

a plurality of transverse engagement grooves formed inside of the engagement slot, and;

the engagement grooves formed to releasably engage the front edge of the free end of the top portion.

2. The medical clamp of claim 1, including an alignment ramp formed on the inside surface of the free end of the engagement end preceding the engagement slot.

3. The medical clamp of claim 1, including a tubing hole formed in the spring portion, a tubing hole formed in the engagement portion, a top cleat formed on the inside surface of the top portion and a bottom cleat formed on the inside surface of the bottom portion.

4. The medical clamp of claim 1, including a thumb well formed on the outside surface of the free end of the top portion.

5. The medical clamp of claim 1, including a textured thumb pattern formed on the outside surface of the free end of the top portion.

6. The medical clamp of claim 1, including a textured finger grip formed on the outside surface of the bottom portion.

* * * * *